United States Patent [19]

Sternberg

[11] Patent Number: 4,935,142
[45] Date of Patent: Jun. 19, 1990

[54] APPARATUS FOR RETAINING VARIABLE NUMBER OF SHEET MEMBRANE ELEMENTS AND A METHOD FOR THE USE THEREOF

[75] Inventor: Shmuel Sternberg, Lexington, Mass.
[73] Assignee: Memtek Corporation, Billerica, Mass.
[21] Appl. No.: 370,609
[22] Filed: Jun. 23, 1989
[51] Int. Cl.⁵ .............................................. B01D 13/00
[52] U.S. Cl. .................... 210/634; 210/645; 210/649; 210/321.75; 210/321.84
[58] Field of Search ........ 210/634, 641, 644, 645–647, 210/649–654, 321.6, 321.62, 321.64, 321.72, 321.75, 321.85, 321.84

[56] References Cited

U.S. PATENT DOCUMENTS

| | | | |
|---|---|---|---|
| 4,197,207 | 4/1980 | Karn | 210/321.75 |
| 4,204,963 | 5/1980 | Bischof et al. | 210/321.84 |
| 4,761,229 | 8/1988 | Thompson et al. | 210/321.82 |

Primary Examiner—Frank Sever
Attorney, Agent, or Firm—Hale and Dorr

[57] ABSTRACT

Provided, is a membrane unit which can sealably accommodate a variable plurality of stacked planar membrane elements.

21 Claims, 3 Drawing Sheets

APPARATUS FOR RETAINING VARIABLE NUMBER OF SHEET MEMBRANE ELEMENTS AND A METHOD FOR THE USE THEREOF

BACKGROUND OF THE INVENTION

This invention relates generally to the field of fluid flow in porous media and more specifically to an apparatus (and a method for the use thereof) for retaining a stack of a variable number of sheet membrane elements, such as filter papers, in the same device while achieving adequate sealing capacity regardless of the number of filter elements in the stack.

A number of applications that require flow through porous media employ a variable number of sheet filter elements, such as filter papers in a stack. A notable example is harvesting biological materials, such as antigens, monoclonal antibodies, virus particles, lymphokines and enzymes by using an affinity binding segregation method. Typically, a filter substrate of paper or other microporous sheet is treated with a substance designed to bond with the substances to be removed from the fluid. The substance with which the filter sheet is treated is referred to as the "ligand." The substance to be removed from the fluid is referred to as the "ligate". The fluid that contains the ligate is brought into contact with the sheet bearing the ligand population. Under suitable conditions, the ligands will bind to the ligates passing therethrough. After a high percentage of the ligand elements of an individual membrane media have bonded to a ligate, the capacity of that particular membrane media may be reached. The membrane sheet still retains its microporous capacity and thus will permit the relatively free flow of fluid therethrough, even after virtual total bonding of the ligands associated with that membrane sheet. It is desirable to be able to stack a number of individual membrane sheets in series to remove a higher percentage of ligate from the solution passing through the membranes. Thus, with a single pass through of solution, a higher yield may be obtained.

During the flow of fluid through the membrane sheet, it is necessary to insure that the fluid flows through the sheet and past the ligands, rather than around a sheet's edges. Therefore, a sealing mechanism must seal off the edges of the membrane sheet or sheets from the fluid flow. In the case of a device capable of holding a variable number of membrane sheets, the sealing mechanism must adequately seal against leakage around the edges of the membrane sheets regardless of the number of sheets used.

After the ligand and ligate associate on the sheet, it is necessary to wash from the sheets any other particles that are not desired. Other particles, which would not be bound to any portion of the membrane sheet, might have become lodged in various microscopic nooks and crannies of the membrane sheet and the vessel. A typical method of washing the undesired particles from the membrane sheets is to flush pure water or another carrier liquid, e.g. buffers, over and through the sheets. The ligand and ligate association is strong enough so that they would not be separated during this mechanical washing. It has been found that it is beneficial to wash the membrane sheet in both the direction of original flow and in a back flow direction, in order to maximize the likelihood that undesired particles will be removed from wherever they may be lodged. Thus, it is necessary that the method of sealing the variable number of membrane sheets adequately seals against leakage when flow is applied in both the forward and backward direction.

Known devices of the prior art with respect to this type of a filtration or particle harvesting method are not capable of sealing a variable number of membrane sheets because the seal structure is sized to accommodate only a fixed number of filter elements, typically a single layer. Further, these known devices cannot be flushed in both directions. All known devices are made for filtration and for that purpose they are adequate. The vessel of this invention provides uniform distribution of fluid over the entire membrane surface area--a different application from simple filtration. It is, however, useful in filtration to achieve uniform surface distribution.

OBJECTS OF THE INVENTION

Thus, the objects of the invention are to provide a vessel for retaining a variable number of membrane sheets where:

a variable number of membrane sheet elements may be used without affecting the sealing integrity of the unit;

the unit may be flushed in both directions without loss of integrity of the seal;

the sheet may be flushed in both directions without requiring removal of the sheet and reorienting it.

SUMMARY OF THE INVENTION

In the present invention, a membrane unit for two direction fluid flow through a variable plurality of sheet membrane elements has a cup element and a cap element. The cup element has a channel for fluid flow having a first and second port. A membrane retention chamber is bounded radially by a circumferential wall and axially by a substantially planar surface pierced by the first port. The cap element has a membrane clamping member and a cap channel for fluid flow, which connects a first cap port to a second cap port. The membrane clamping member has an outward facing circumferential clamping wall sized to fit within the circumferential retention wall that bounds the membrane retention chamber and an outward facing chamfer edge sloping radially inward from the outward facing circumferential clamping wall. The chamfer edge slopes to a surface, which is pierced by the second port of the cap channel. An O-ring contacting and concentric with the circumferential wall of the cup element and the chamfer edge of the membrane clamping member rests on top of the stack of membranes. The membranes are stacked in the filter retention chamber on top of the planar surface pierced by the first port. The O ring is trapped in the triangular annular space bounded on the outside by the circumferential wall of the membrane retention chamber, on the inside by the chamfer edge of the membrane clamping member and on the bottom by the top membrane. Because of the chamfer, as additional membrane sheets are added, the O ring maintains the seal.

The membrane retention member may be secured to the cup element by any of several well known methods. Mating threads may be provided on the circumferential retention wall of the cup element and the circumferential clamping wall of the cap element; the circumferential wall of the cap may fit snugly within that of the cup and an external clamp and spring may be used to maintain pressure. Other methods will be apparent to one of ordinary skill in the art.

It will be understood that the O ring seal in addition to sealing a variable number of filter sheets, will also seal against flow in either direction.

The method of the present invention, for segregating a ligate from a fluid using the affinity technique comprises the steps of providing a plurality of sheet membrane elements that bear a ligand population having a known affinity for the ligate, providing an apparatus as discussed above, placing the plurality of membrane elements within one membrane retention chamber and securing the cap element to the cup element. The fluid that bears the ligate is introduced to the unit through an input port, and flows over the surface of and through the membrane element. After the fluid has passed through the desired number of times (or units) the unit is flushed with a rinse fluid to remove unbound substances from said membrane. The rinse fluid is flushed through the unit in both the forward direction of fluid flow and in the reverse, backward direction. Subsequently, the ligand can be removed from the ligate by chemical or other appropriate means. Alternatively, the ligand/ligate complex may be removed as a unit from the membrane.

The foregoing described invention will be more fully understood in connection with the following detailed discussion of a preferred embodiment and the figures of the drawings.

DETAILED DISCUSSION OF A PREFERRED EMBODIMENT OF THE INVENTION

Figure 1:
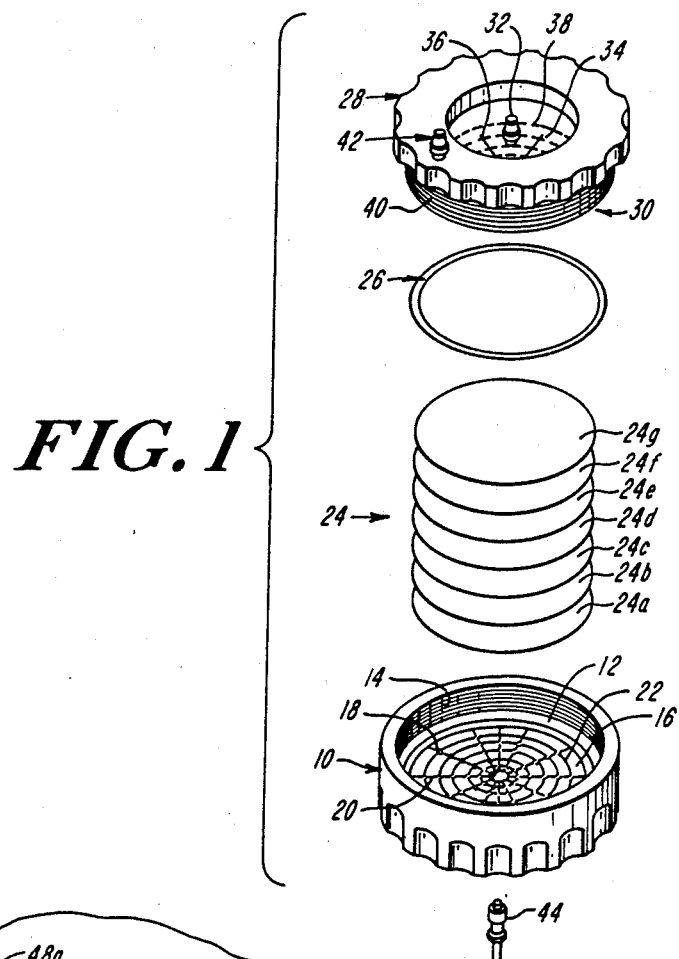
FIG. 1 is a schematic perspective exploded view of a preferred embodiment of the invention.

The general structure of the claimed invention is shown in FIG. 1, a schematic perspective exploded view of a preferred embodiment. Cup element 10 is shown, having a membrane retention chamber 12 bounded radially by circumferential retention chamber wall 14 and axially by a substantially planar membrane support surface 16. Cup element 10, and all elements of the membrane units that will come in contact with the test fluid, is of a material, such as acrylic. A first cup port 18 opens into planar surface 16. Radial channels 20 and circumferential channels 22 are provided on membrane support surface 16 to conduct fluid to port 18 when fluid flows in the forward flow direction. A plurality of sheet membrane elements 24 (24a–24g) are retained in membrane retention chamber 12. O-ring 26 rests on top of the upper membrane 24, in this case membrane 24g.

A cap element 28 has a filter clamping member 30 for engaging the O-ring 26 and membranes 24. An inlet fitting 32 is provided for introducing the fluid to be flowed through the unit. The bottom surface 34 (shown in phantom) of cap element 28 has radial channels 36 and circumferential channels 38 arranged in the same manner as those on surface 16 of cup element 10, for channeling the fluid from a first port (not shown) over the entire surface of the stack of sheets 24 when fluid flows in the forward flow direction.

Cap element 28 has a circumferential, outward facing clamping wall 40 sized to fit within and seal loosely with circumferential retention chamber wall 14 of cup element 10. In the embodiment shown in FIG. 1, clamping wall elements 40 and retention chamber wall 14 are threaded so that they may be screwed together to a variable axial extent. A vent 42 is provided in cap element 28 to allow any air which had been trapped within the sheets 24 and other spaces within the assembly chamber to escape, as liquid is introduced into inlet fitting 32. An exit fitting 44 is provided in association with cup element 10 and engages a second cup port (not shown). (See 76 of FIG. 3a.)

Figure 2:
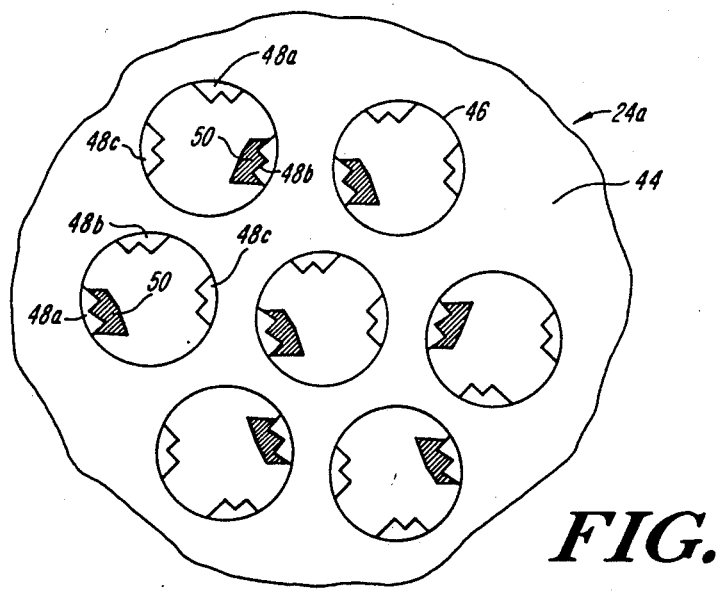
FIG. 2 is a schematic drawing of a portion of a type of membrane media suitable for use in a preferred embodiment of an invention, showing schematically the ligand and ligate bonding mechanism.

Turning now to FIG. 2, the mechanism of operation of the molecular affinity separation sheets 24 is illustrated. Sheet 24a is a cellulosic, microporous substrate 44. In FIG. 2, a portion of a sheet 24a is shown with pores 46 shown schematically. In FIG. 2, seven pores are shown. For a membrane disk 76 millimeters in diameter, approximately 10 billion pores are present. In FIG. 2, each pore 46 is shown to have associated therewith three ligand molecules 48a, 48b and 48c. Arbitrarily selected ligands 48 have associated therewith a ligate molecule 50. The membrane discs 24g are available with various types of ligand molecules attached. Membrane discs suitable for use in connection with the claimed invention are available from Memtek Corporation of 28 Cook Street, Billerica, Mass. 01821 (508) 667-2828 and are sold under the trade name "MAC TM Discs". The sheets are hydrophilic. Examples of available ligands are recombinant Protein A and G, antigens, monoclonal antibodies, virus particles, lymphokines and enzymes. A typical binding chemistry between the membrane and the ligand involves covalent coupling of the amino group of a ligand to aldehyde groups on the affinity membrane matrix. The coupling will occur at a pH of from 8.0 to 9.5 with optimum ligand to membrane binding at pH 9.3. In fact, any molecule containing an amino group can be bound to the membrane. Other molecules can be bound by manipulation of the membrane surface chemistry to yield amino, carboxy or hydroxy functionalities, among others.

Although FIG. 2 is schematic only, it illustrates the fact that even if all of the ligands on a membrane sheet bind to ligates in the solution to be treated, virtually no change in the porosity of the membrane sheet arises, due to the relatively extremely large size of the pores as compared to the ligand/ligate complex. Thus, it is possible to stack multiple sheets, all of which will be exposed to fluid that bears ligate.

It will be readily understood that the capacity of a given configuration of membrane discs depends upon the surface area of the filter, concentration of ligands per square centimeter, binding affinity of the ligands to the ligate, and the number of layers of membranes used.

An example of a sheet separation using the apparatus of the invention as shown in FIG. 1 was generated using a sheet holder holding 10 discs, 76 millimeters in diameter. The ligand was a recombinant protein designated as Protein A, sold by Repligen Co., of Cambridge, Mass., carried by a membrane sold by Memtek Corporation identified above. The separation sample was Human IgG (gamma fraction) 25 ml, with a concentration of 10 mg/ml. A syringe with a repeatable adaptor was connected to inlet fitting 32 and ten passes were made. Over a total time of ten minutes, 63.5 mg of Human IgG were separated.

Figure 3A:
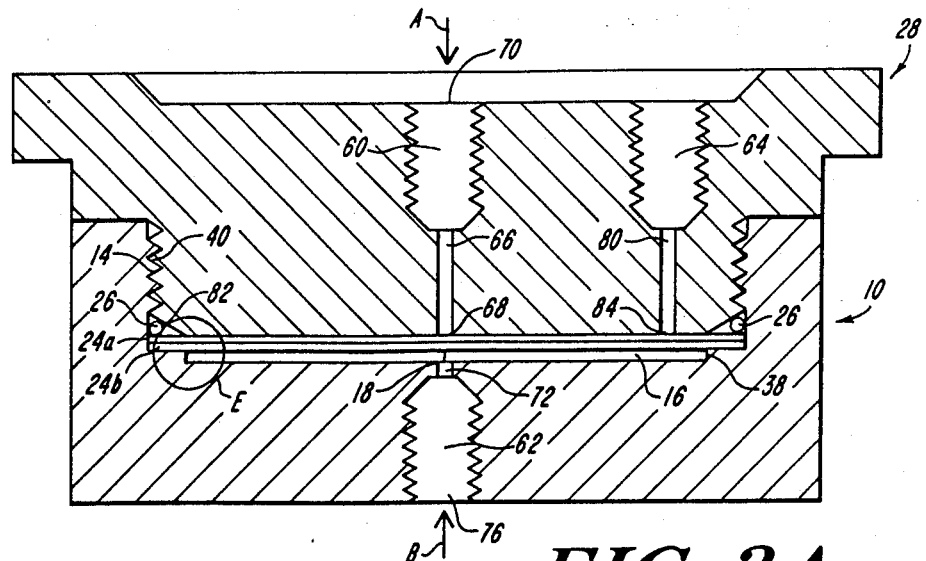
FIG. 3a is a schematic cross-sectional view of a preferred embodiment of the invention adjusted to retain a relatively small number of filter sheets.
Figure 3B:
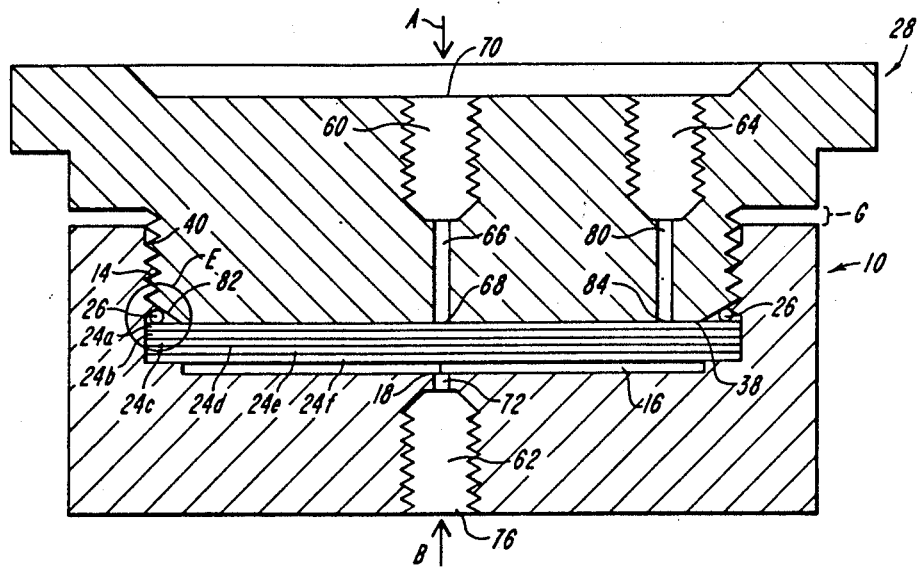
FIG. 3b is a schematic cross-section of a preferred embodiment of the invention adjusted to retain a relatively large number of filter sheets.

Turning now to FIGS. 3a and 3b, the manner in which the seal of the claimed invention accommodates a variable number of filter sheets 24 will be understood. Elements shown in FIG. 3a identical to elements shown in FIG. 1 are referenced by identical reference numerals. As shown in FIG. 3a, cap element 28 has been connected to cup element 10 by threading clamping wall 40 and retention chamber wall 14 together. Second port 70 is provided with a threaded hole 60, sized to receive inlet fitting 32 (not shown in FIG. 3a). A suitable fitting for these elements is a leur-lock. Similarly, second port 76 is provided with a threaded hole 62, sized to receive outlet fitting 44 (not shown in FIG. 3a). Threaded hole 64 is sized to receive vent fitting 42 (not shown in FIG. 3a). Cap channel 66 connects threaded hole 60 with first port 68 from cap element 28, thereby placing second port 70 in fluid communication with first port 68.

Cup channel 72 connects first port 18 of cup element 10, through threaded hole 62 to second port 76 of cup element 10, thereby permitting fluid to pass entirely through the cup element 10. Channel 80 connects venting fitting 42, through hole 64 and vent port 84 to the planar surface 38 of cap element 28 thereby allowing air that would originally be trapped within the membrane sheets 24 to escape up through the vent as fluid is introduced to the sheets through inlet fitting 32 and input port 70 in the direction of Arrow A.

FIG. 3a shows a systems using two membrane sheets 24a and 24b. These sheets rest on top of support surface 16. Support surface 16 may be formed integrally with cup element 10, or may be formed separately.

Figure 3C:
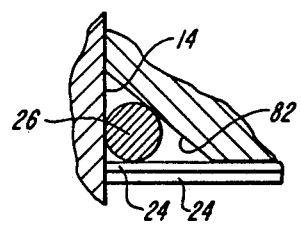
FIG. 3c is an enlarged view at E of FIGS. 3a and 3b to show the cooperation of the elements that effect the fluid seal.

As shown in FIG. 3a and 3c (enlarged), the cap element 28 is screwed all the way down to tightly clamp membrane sheets 24a against cup element 10. O-ring 26 forms a seal to prevent fluid from passing around the perimeter of membrane sheets 24. Thus, fluid is forced over the ligand bearing portions of the surface area of the sheets 24. The O-ring 26 seals against three surfaces to insure the seal. It seals against beveled chamfer 82 of membrane clamping member 30. As membrane clamping member 30 presses against the O-ring 26, the O-ring 26 also seals against circumferential retention chamber wall 14 of cup element 10 and to the upper most membrane sheet 24a.

Turning now to FIG. 3b, the relationship of the elements of the invention assume when securing a relatively larger number of membrane discs is shown. The elements shown in FIG. 3b are identical to those shown in FIG. 3a, except that FIG. 3b shows additional membrane sheets 24c–24f and the cap element 28 is not threaded entirely down into cup element 10, but rather is backed up to accommodate the additional membranes, as is evident from the gap at G. It will be understood, however, that the sealing arrangement among O-ring 26, retention chamber wall 14, beveled chamfer edge 82 and upper membrane sheet 24a remains the same as it is shown in FIGS. 3a and 3c. The triangular cross-section annular space around the perimeter of the chamber remains the same size and thus the O-ring 26 adequately seals against fluid flow around the perimeter of the membranes 24.

Depending upon the application, the maximum number of membrane discs that may be used may depend upon the porosity of each, the fluid flow resistance of each, etc. However, with respect only to limitations imposed by the holder assembly on the number of membrane discs, it will be understood that the number can be widely varied by suitable adjustment of the axial extent of retention chamber wall 14, clamping wall 40 and the length of the threaded portion of retention chamber wall 14 relative to the length of the unthreaded portion, as compared to the axial extent of the beveled edge 82.

Figure 4B:
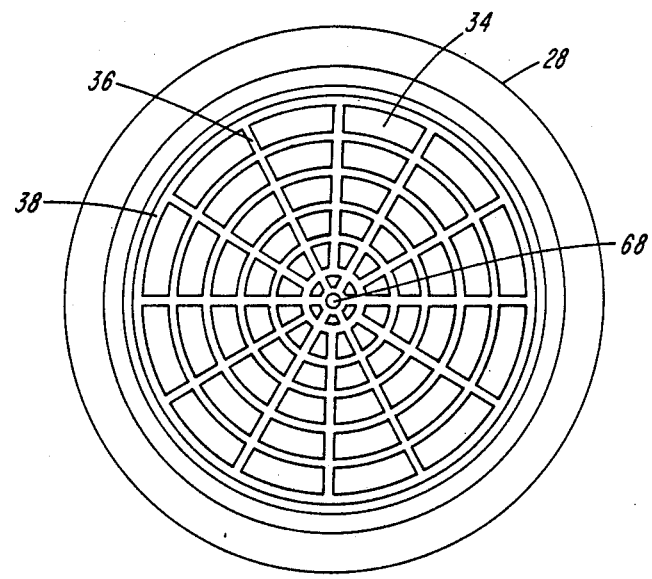
FIG. 4 is a plan view of a channeled planar surface that is used both in the filter retaining cup element and the cap element.
Figure 4A:
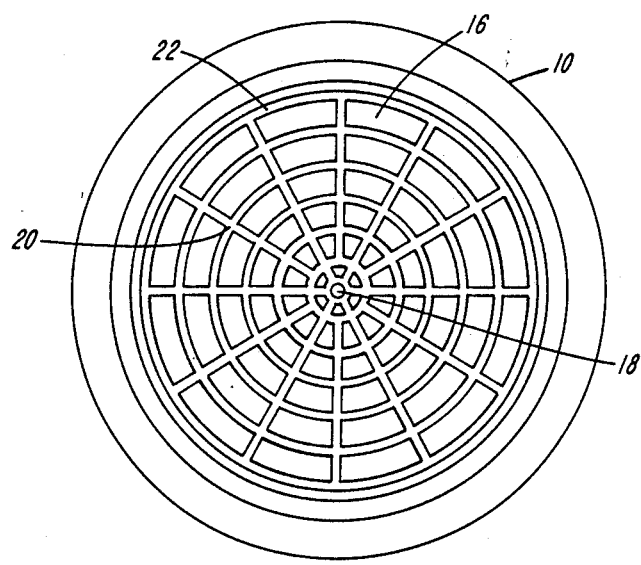

As shown in FIGS. 1 and FIG. 4a and 4b, membrane support surface 16 of cup element 10 and membrane contacting surface 34 of cap element 28 are provided with a central port 18, 68 (respectively) and radial 20, 36 (respectively) and circumferential 22, 38 (respectively) channels. In both cases 16, 34, the channelled surfaces face and contact the stack of membrane sheets 24. That is for the cup element surface 16, the channels are on the surface facing upward, as shown in FIG. 1 and for the cap element surface 34 the channels are on the surface facing downward.

Thus, for example, in connection with flow in the direction of Arrow A (FIG. 3a) as fluid is introduced from inlet fitting 32 through first cap port 68 it will be urged outward along radial grooves 36 and around the circumferential grooves 38 of increasing diameter, thus spreading out uniformly over the surface of membrane sheets 24.

Conversely, as fluid passes through the bottommost membrane as shown in FIG. 3a, e.g. 24b, it contacts the entire area of surface 16. Fluid flows around circumferential channels 22 to radial channels 20, and along radial channels 20 to first cup port 18. The fluid flows from first cup port 18 along channel 72, through hole 62 and out second cup port 76 through exit fitting 44.

As has been mentioned, it is necessary to flush the chamber with a sterile solution to remove unwanted particles not bound to the ligand, from the various interstices in the sheet and assembly structure. Flushing is conducted in both the direction of test solution flow (in the direction of Arrow A of FIG. 3) and also in the opposite direction (the direction of Arrow B in FIG. 3a). Thus, it is beneficial to have the grooved configuration discussed above on both the surfaces 16 and 34 because they perform the same functions, depending on whether the flow is forward or backward. However, this is not a necessary feature of the invention in its broadest aspect.

The claimed invention is useful in other filtering and separation applications, other than membrane affinity chromatography. For instance, it may be useful in normal mechanical filtration systems and also would be useful in connection with ion exchange sheet separation techniques. The flow distribution and stacking advantages mentioned above are just as important in the ion exchange case where, the ligand and the ligate simply carry opposite electrical charges. Thus, an affinity exists between them and the ligate in the fluid will bind to the ligand on the membrane.

In general, the membrane assembly is useful in any application where a ligand can be immobilized in a mechanical membrane past or through which will flow a fluid bearing a ligate, which ligate has a binding affinity with the ligand of a sufficient strength to result in binding of the ligate to the ligand in the fluid flow environment. The affinity may be due to steric phenomena, such as molecular, and immunosorption, or enzyme-coenzyme, charge, chemical, hydrophobic, magnetic or mechanical phenomena. Steric phenomena are those whereby the ligand and ligate bond due to the conformance of regions on each with the other with respect to electro-chemical interactions.

It is also possible to remove the ligate/ligand complex from the membrane as a unit. One means by which this may be accomplished is to attach a ligand to a membrane and to attach a ligate to the first ligand, which ligate acts as a ligand for a second ligate. After the three element association of first ligand-first ligate-second ligate is formed and segregated from the fluid, the bond between the first ligand and the first ligate may be broken and the first ligate/second ligate complex may be collected. An example of a first ligate/second ligate complex that may be created in this manner is a complex of biotin and avidin, useful for amplification of chemical and enzymatic signals.

Further, rather than having a circular circumference, the assembly may have any other circumference that will permit use of an O-ring, such as rectangular or oval. In the latter two cases, however, alternative clamping means, rather than screw threads must obviously be used. Suitable alternative clamping means include a hinged spring clamp for maintaining pressure of the membrane clamping member against the membranes.

The foregoing should be considered to be illustrative and not to be limiting in any manner. Having thus described the invention, what is claimed is:

1. A membrane unit for two direction fluid flow and affinity binding through a variable plurality of sheet membrane elements, said unit variable comprising:
   a. a cup element having a chamber for retaining said plurality of membrane elements, bounded radially by a circumferential retention wall and axially by a substantially planar surface;
   b. a cap element having a membrane clamping member having:
      (i) an outward facing circumferential clamping wall sized to fit within the circumferential retention wall which bounds the membrane retention chamber;
      (ii) an outward facing chamfer edge sloping radially inward from the outward facing clamping wall; and
      (iii) a surface for clamping against said plurality of membrane elements;
   c. an O-ring contacting and concentric with the cup element and the membrane clamping member having an outside circumferential extent substantially co-extensive with the circumference of the circumferential retention wall and an inside circumferential extent greater than the smallest circumferential extent of the chamfer edge surface; and
   d. means for clamping the cup element to the cap element, retaining the O-ring and the membrane elements therebetween.

2. The membrane unit of claim 1 where the circumferences of the retention wall and the clamping walls are circular.

3. The membrane unit of claim 2, said cup element further comprising a cup channel for fluid flow, having a first and a second port, said first port piercing said substantially planar surface.

4. The membrane unit of claim 3, said cap element further comprising a cup channel for fluid flow, having a first and a second port, said first port piercing said surface for clamping said membrane elements.

5. The membrane unit of claim 4, said substantially planar cup surface comprising a plurality of intersecting circumferential and radial channels, said radial channels meeting at said first port of said cup channel.

6. The membrane unit of claim 4, said clamping surface comprising a plurality of intersecting circumferential and radial channels, said radial channels meeting at said first port of said cap channel.

7. The membrane unit of claim 4, said cap element further comprising a vent channel, having a first port piercing said clamping surface and a second port communicating with a zone at atmospheric pressure.

8. The membrane unit of claim 1, where the circumferences of the retention wall and the clamping walls are rectangular.

9. The membrane unit of claim 1, where the circumferences of the retention wall and the clamping walls are oval.

10. The membrane unit of claim 1, wherein said means for clamping the cup element to the cap element comprises mating threads on said retention and clamping walls.

11. The membrane unit of claim 1, wherein said means for clamping the cup element to the cap element comprises a hinged spring clamp.

12. The membrane unit of claim 1, wherein said cup and cap elements are of an acrylic material.

13. An affinity binding membrane unit for ion exchange segregation of ligate having an electrical charge of a known polarity employing two direction fluid flow through a variable plurality of sheet membrane elements, said unit comprising:
   a. a variable plurality of sheet membrane elements that bear a ligand population, each ligand having an electrical charge of a known polarity;
   b. a cup element having a chamber for retaining said plurality of membrane elements, bounded radially by a circumferential retention wall and axially by a substantially planar surface;
   c. a cap element having a membrane clamping member having:
      (i) an outward facing circumferential clamping wall sized to fit within the circumferential retention wall which bounds the membrane retention chamber;
      (ii) an outward facing chamfer edge sloping radially inward from the outward facing clamping wall; and
      (iii) a surface for clamping against said plurality of membrane elements;
   d. an O-ring contacting and concentric with the cup element and the membrane clamping member having an outside circumferential extent substantially co-extensive with the circumference of the circumferential retention wall and an inside circumferential extent greater than the smallest circumferential extent of the chamfer edge surface; and
   e. means for clamping the cup element to the cap element, retaining the O-ring and the membrane elements therebetween.

14. The segregation unit of claim 13 where the circumferences of the retention wall and the clamping walls are circular.

15. The segregation unit of claim 13, wherein said means for clamping the cup element to the cap element comprises mating threads on said retention and clamping walls.

16. A method of segregatinq a ligate constituent of a fluid using affinity binding comprising the steps of:
 a. providing plurality of sheet membrane elements which bear a ligand population having affinity for the ligate;
 b. providing a means for retaining a variable plurality of said membranes having:
  i. a cup element having a chamber for retaining said plurality of membrane elements, bounded radially by a circumferential retention wall and axially by a substantially planar surface;
  ii. a cap element having a membrane clamping member having:
   (A) an outward facing circumferential clamping wall sized to fit within the circumferential retention wall which bounds the membrane retention chamber;
   (B) an outward facing chamfer edge sloping radially inward from the outward facing clamping wall; and
   (C) a surface of clamping against said plurality of membrane elements;
  iii. an O-ring contacting and concentric with the cup element and the membrane clamping member having an outside circumferential extent substantially co-extensive with the circumference of the circumferential retention wall and an inside circumferential extent greater than the smallest circumferential extent of the chamfer edge surface; and
  iv. means for clamping the cup element to the cap element, retaining the O-ring and the membrane elements therebetween;
 c. securing said membranes in said membrane unit.
 d. passing said fluid through said membrane unit and over the surface of and through said membrane elements, thus binding ligate to said ligand population; and
 e. flushing a rinse fluid through said membrane unit in both forward flow and backward flow directions to remove unbound substances from said membrane elements; and 17. The method of claim 16, where said ligate has an electrical charge affinity for said ligand.

18. The method of claim 16, where said ligate has a steric affinity for said ligand.

19. The method of claim 16 where said ligate has a magnetic affinity for said ligand.

20. The method of claim 16 comprising further the step of removing said ligate from said ligand.

21. A membrane unit for two direction fluid flow through a variable number of sheet membrane elements, said unit comprising:
 a. a cup element having a chamber for retaining said membrane variable number of element(s), bounded radially by a circumferential retention wall and axially by a substantially planar surface;
 b. a membrane clamping member having:
  (i) an outward facing circumferential clamping wall sized to fit within the circumferential retention wall which bounds the membrane retention chamber;
  (ii) an outward facing chamber edge sloping radially inward from the outward facing clamping wall; and
  (iii) a surface for clamping against said membrane element(s); and
 c. a resilient annular sealing member contacting and concentric with the cup element and the membrane clamping member having an outside circumferential sealing surface engaging the circumferential retention wall, an inside circumferential sealing surface engaging the chamfer edge surface, and an axial circumferential sealing surface engaging the membrane element(s).

* * * * *